(12) United States Patent
Iwata (10) Patent No.: US 7,752,896 B2
(45) Date of Patent: Jul. 13, 2010

(54) SPECIMEN PRETREATING DEVICE AND PROBE USED THEREFOR

(75) Inventor: Yosuke Iwata, Kyoto (JP)

(73) Assignee: Shimadzu Corporation, Kyoto-shi, Kyoto (JP)

( * ) Notice: Subject to any disclaimer, the term of this patent is extended or adjusted under 35 U.S.C. 154(b) by 620 days.

(21) Appl. No.: 11/661,083

(22) PCT Filed: Aug. 30, 2005

(86) PCT No.: PCT/JP2005/015734
§ 371 (c)(1),
(2), (4) Date: Feb. 26, 2007

(87) PCT Pub. No.: WO2006/025367
PCT Pub. Date: Mar. 9, 2006

(65) Prior Publication Data
US 2008/0048664 A1   Feb. 28, 2008

(30) Foreign Application Priority Data
Aug. 30, 2004   (JP) .............................. 2004-250729

(51) Int. Cl.
*B01D 15/08* (2006.01)
*G01N 30/84* (2006.01)

(52) U.S. Cl. ..................... 73/61.55; 73/61.52; 210/101; 210/198.2; 422/70

(58) Field of Classification Search ................ 73/61.52, 73/61.54, 61.55, 61.57
See application file for complete search history.

(56) References Cited

U.S. PATENT DOCUMENTS 4,977,785 A * 12/1990 Willoughby et al. ..... 73/863.12

6,672,344 B1 * 1/2004 Stokes et al. ................... 506/40
2004/0238427 A1 * 12/2004 Maruyama et al. ....... 210/198.2

FOREIGN PATENT DOCUMENTS

| JP | 49-28064 | 7/1974 |
|----|----------|--------|
| JP | 59-24250 | 2/1984 |
| JP | 64-5163  | 1/1989 |

(Continued)

OTHER PUBLICATIONS

Japanese Office Action mailed Oct. 7, 2008, issued in JP 2006-532707 (Dispatch No. 6074723).

*Primary Examiner*—Daniel S Larkin
(74) *Attorney, Agent, or Firm*—Edwards Angell Palmer & Dodge LLP (57) ABSTRACT

A specimen pretreating device which includes a micro scale or nano scale high-performance liquid chromatograph having a capillary column (2), a probe (1) integrally formed at the tip of the capillary column (2), and an additive feeding flow passage (16). The probe (1) is formed in a multi-tube structure in which a plurality of tubes are disposed on the same axis. The innermost tube is located at the tip of the capillary column (2), and one of the outer tubes is used as an additive supply tube converging an additive solution to an eluent solvent eluted from the capillary column (2) to form liquid drops including the eluent solvent and an additive, and the liquid drops are released from the tip of the probe (1). The specimen is not diffused since a detector is not present in the flow passage.

20 Claims, 7 Drawing Sheets

FOREIGN PATENT DOCUMENTS

| | | |
|---|---|---|
| JP | 1-212350 | 8/1989 |
| JP | 05-256749 A * | 10/1993 |
| JP | 8-211019 | 8/1996 |
| JP | 08-304373 | 11/1996 |
| JP | 3099866 U * | 12/2003 |
| JP | 2004-184149 | 7/2004 |
| JP | 2005-30969 | 2/2005 |
| JP | 2005-195411 | 7/2005 |
| JP | 2005-201828 | 7/2005 |
| WO | WO 02/062475 | 8/2002 |

* cited by examiner

SPECIMEN PRETREATING DEVICE AND PROBE USED THEREFOR

BACKGROUND OF THE INVENTION

1. Field of the Invention

The present invention relates to a probe used for dropping a sample solution eluted from a liquid-transporting mechanism such as a high-performance liquid chromatograph as droplets from the tip thereof onto a plate such as a micro-plate or a sample plate, and a sample pretreatment apparatus including such a probe.

2. Description of the Related Art

Conventionally, in a case where an eluant separated by a separation column of a high-performance liquid chromatograph is automatically dropped on to a sample plate, for example, for a MALDI-TOF-MS (Matrix assisted laser desorption ionization time of flight mass spectrometry) so as to be fractioned and collected, a component to be measured is separated by a high-performance liquid chromatograph (HPLC) and connected to a UV detector from the tip of the separation column through a pipe (see Japanese Unexamined Patent Publication No. 2004-184149).

Normally, the amount of a droplet to be dropped on to a sample plate for the MALDI is 2 µL at the most, and in order to allow such a small amount of a droplet to drop, the liquid chromatograph uses not a normal flow rate of 1 mL/min, but a micro-scale of 5 µL/min or a nano-scale of 200 nL/min, as the flow-rate scale. This is because in an attempt to drop at every 1 µL at 1 mL/min, spots (dropping) are for every 0.001 min, and this operation is virtually impossible.

In a case of a normal flow-rate scale, a pipe having an inner diameter of about 0.3 mm is used; however, in order to ensure a proportional relationship between the flow-rate scale and the pipe inner diameter and to limit the dispersion of a component separated by a separation column to a minimum level, the pipe inner diameter is further narrowed to 1.5 µm in the micro-scale, and to 60 nm in the nano-scale.

However, in actuality, the pipe having an inner diameter in a range from 20 to 50 µm is used by taking into consideration clogging of the pipe due to contamination (foreign matters). For example, upon application of a pipe having an inner diameter of 50 µm, the pipe capacity becomes 1 µL when the pipe length is 500 mm.

In a case of the normal flow-rate scale, the size of the pipe capacity corresponds to a pipe capacity of 5 mL with respect to the flow rate of 1 mL/min, and due to such a large pipe capacity, the target component separated by the separation column is dispersed. In a case where the analysis is carried out by using a flow rate in the nano-scale, the influence caused by the pipe capacity becomes more conspicuous.

In a case of using the MALDI-TOF-MS, there is a demand that ideally, a single target component, separated by the high-performance liquid chromatograph, should be dropped on to a single well.

Such a demand is given not only in the preparation of a sample for the MALDI-TOF-MS, but also in the addition of an additive such as a reaction solution to an eluent from the high-performance liquid chromatograph.

SUMMARY OF THE INVENTION

In a case where a UV detector is installed behind the separation column, upon analysis in the micro-scale, each droplet tends to be spotted on a well with a peak width wider than the peak width that is confirmed by the UV detector. Upon application to an analysis in the nano-scale, the expanded peak on the well further increases by several times, making separation by the use of the high-performance liquid chromatograph meaningless.

An object of the present invention is to prevent dispersion caused by the pipe capacity.

A probe in accordance with the present invention, which has a multi-pipe structure in which a plurality of pipes are placed concentrically, is provided with: a pipe on the innermost side that forms a tip of a capillary column used for separation in a micro-scale or nano-scale high-performance liquid chromatograph; and one of the outside pipes that is prepared as an additive supplying pipe used for allowing an additive solution to be joined to an eluent from the capillary column, and in this structure, droplets containing the eluent and the additive are formed and dropped from the tip of the probe.

A sample pretreatment apparatus in accordance with the present invention is provided with: a micro-scale or nano-scale high-performance liquid chromatograph having a capillary column; a probe, integrally formed on the tip of the capillary column, which has a multi-pipe structure in which a plurality of pipes are placed concentrically, and has a pipe on the innermost side that forms a tip of the capillary column and one of the outside pipes that is prepared as an additive supplying pipe used for allowing an additive solution to be joined to an eluent from the capillary column, so that droplets containing the eluent and the additive are formed and dropped from the tip of the probe; and an additive supplying flow path used for supplying an additive to the additive supplying pipe.

With respect to the additive solution, various solutions may be used, and one preferable example is a solution for a matrix compound used for preparing a sample for use in an analysis in mass spectrometry by a Matrix assisted laser desorption ionization time of flight method.

One example of the multi-pipe structure is a triple pipe structure, and in that case; the second pipe from the inside is the additive supplying pipe and the pipe on the outermost side is a second mobile phase supplying pipe through which the second mobile phase different from the mobile phase in the eluent is allowed to flow, or the second pipe from the inside is a second mobile phase supplying pipe through which the second mobile phase different from the mobile phase in the eluent is allowed to flow; and the pipe on the outermost side is the additive supplying pipe. In this case, the droplets to be formed contain the eluent, the additive and the second mobile phase.

In one mode of the sample pretreatment apparatus provided with this triple pipe structure is a second mobile phase supplying flow path further installed, the flow path supplies the second mobile phase to the second mobile phase supplying pipe.

For example, upon analyzing protein by using a high-performance liquid chromatograph, a solution containing water and acetonitrile, serving as a mobile phase, is transported while the composition thereof is being varied by a liquid-transporting mechanism of a gradient system. In this high-pressure gradient analysis, the composition of the mobile phase is transferred from a state containing much water component to a state containing much acetonitrile in the composition of the mobile phase. In an apparatus in which: a droplet is formed on the tip of the probe, and when the droplet has reached a predetermined size, the probe or the sample plate is moved in up and down directions to make the droplet come in contact with the sample plate to shift the droplet thereto; the component of the droplet becomes different between a state immediately after the start of distribution and a state immediately before the completion of the distribution.

And, immediately after the start of distribution, much water component is contained, while, immediately before the completion of the distribution, much acetonitrile is contained; therefore, the surface tension of the droplet to be formed on the tip of the probe is varied, resulting in a failure to form a droplet having a uniform size.

Moreover, in a case where a matrix solution is added to an eluent from a capillary column at the tip of the probe so as to be distributed from the tip, a hydrophobic substance such as a fluororesin is often used as the material for the matrix adding pipe of the probe portion so as to prevent the droplets from rising along the matrix adding pipe. For this reason, since the droplet contains much water component immediately after the start of distribution, the droplet is formed on the inner diameter side of the matrix adding pipe; however, since the droplet contains much acetonitrile immediately before the completion of the distribution, the droplet is formed on the outer diameter side of the matrix adding pipe. And, when the volume of the droplets is constant, the outer shapes of droplets formed at the tip of the probe are made different between a state immediately before the start of distribution and a state immediately after the completion of the distribution. In other words, since the droplets formed at the tip of the probe have different heights in the direction toward the sample plate, even in a case of having a sensor used for keeping the distance between the tip of the probe and the sample plate constant, the droplet is not made to come in contact with the sample plate, in particular, in a case where the amount of the droplet is very small, sometimes resulting in a failure to shift the droplet to the sample plate.

Therefore, in a preferable mode in the present invention, the second mobile phase is designed so that, when mixed with the mobile phase in the eluent, it makes the composition of the mobile phase in the droplet constant.

With this arrangement, it becomes possible to suppress changes in the external shape of the droplet due to a change in the composition of the mobile phase, and consequently to carry out stable distributing operations.

With respect to the solvent for the matrix solution, a saturated solution containing water:acetonitrile=1:1 is often used. In a case where the matrix solution is added to an eluent from the separation column at the tip of the probe so that distributing operations are carried out from the tip, if much water is contained in the mobile phase composition immediately after the start of distribution, the matrix in the saturated matrix solution is deposited on the tip of the probe when the mobile phase is mixed with the matrix solution, interfering with stable distributing operations to cause a problem of carry-over due to invasion of the component to be measured into the matrix. However, when the mobile phase composition in the droplet to be formed on the tip of the probe is made constant as described above, it becomes possible to prevent the matrix from depositing on the tip of the probe.

In another preferable mode in the present invention, the pipe on the outermost side of the multiple pipes, which is made to come in contact with the droplets, is made from a hydrophobic material. With this arrangement, it becomes possible to prevent the droplet from adhering to the outer surface of the tip of the probe, and consequently, to spot a uniform droplet onto a sample plate. One preferable example of the hydrophobic material is fluororesin.

Upon manually washing the tip of the probe before fractioning operations, time consuming and complicated operations are required, and the operability is also poor; therefore, in still another mode for the probe of the present invention, the multiple pipes are provided with a washing liquid supplying pipe that is capable of sending a washing liquid used for dissolving deposits from the additive solution on its outermost side.

In a preferable mode for a sample pretreatment apparatus provided with this washing liquid supplying pipe, a washing liquid supplying flow path used for supplying a washing liquid to the washing liquid supplying pipe is further prepared therein.

By preparing the washing liquid supplying pipe in this manner, the matrix compound deposited on the tip of the probe can be automatically removed.

When the washing liquid remains on the probe, it may be removed by using a cloth; however, at this time, since the cloth comes into contact with the probe, the probe position tends to deviate, resulting in inaccurate dropping positions.

Therefore, in a preferable mode for the sample pretreatment apparatus, a gas supplying flow path, which is switched from the washing liquid and supplies a gas used for drying, is further prepared in the washing liquid supplying flow path. By discharging a gas from the tip of the probe to dry and evaporate the residual washing liquid on the tip of the probe after the washing process, the succeeding fractioning processes of a biological sample can be uniformly carried out without deviations in the dropping position of the droplet In still another preferable mode for the sample pretreatment apparatus of the present invention, the following are prepared therein: a plate used for collecting droplets dropped from the probe, a supporting mechanism that shifts the plate or the probe at least up and down directions, a distance measuring means for measuring the distance between the tip of the probe and the plate, and a control unit that controls the shift of the supporting mechanism so as to set the distance between the tip of the probe and the plate to a predetermined distance based upon the results of measurements by the distance measuring means upon dropping droplets from the probe.

By preparing the means for measuring the distance between the tip of the probe and the plate so that the distance is made closer to a predetermined distance, it becomes possible to prevent the distance between the probe and the MALDI plate from becoming too far, or too close to come into contact with each other.

According to the present invention, because the capillary column is extended to the tip of the probe inside the probe, a target component to be fractioned can be spotted on the MALDI plate without being influenced by dispersion caused by the pipes.

BRIEF DESCRIPTION OF THE DRAWINGS

FIG. 4A and FIG. 4B show a time-based change in compositions of a first mobile phase and a second mobile phase.

BEST MODE FOR CARRYING OUT THE INVENTION

Figure 1:
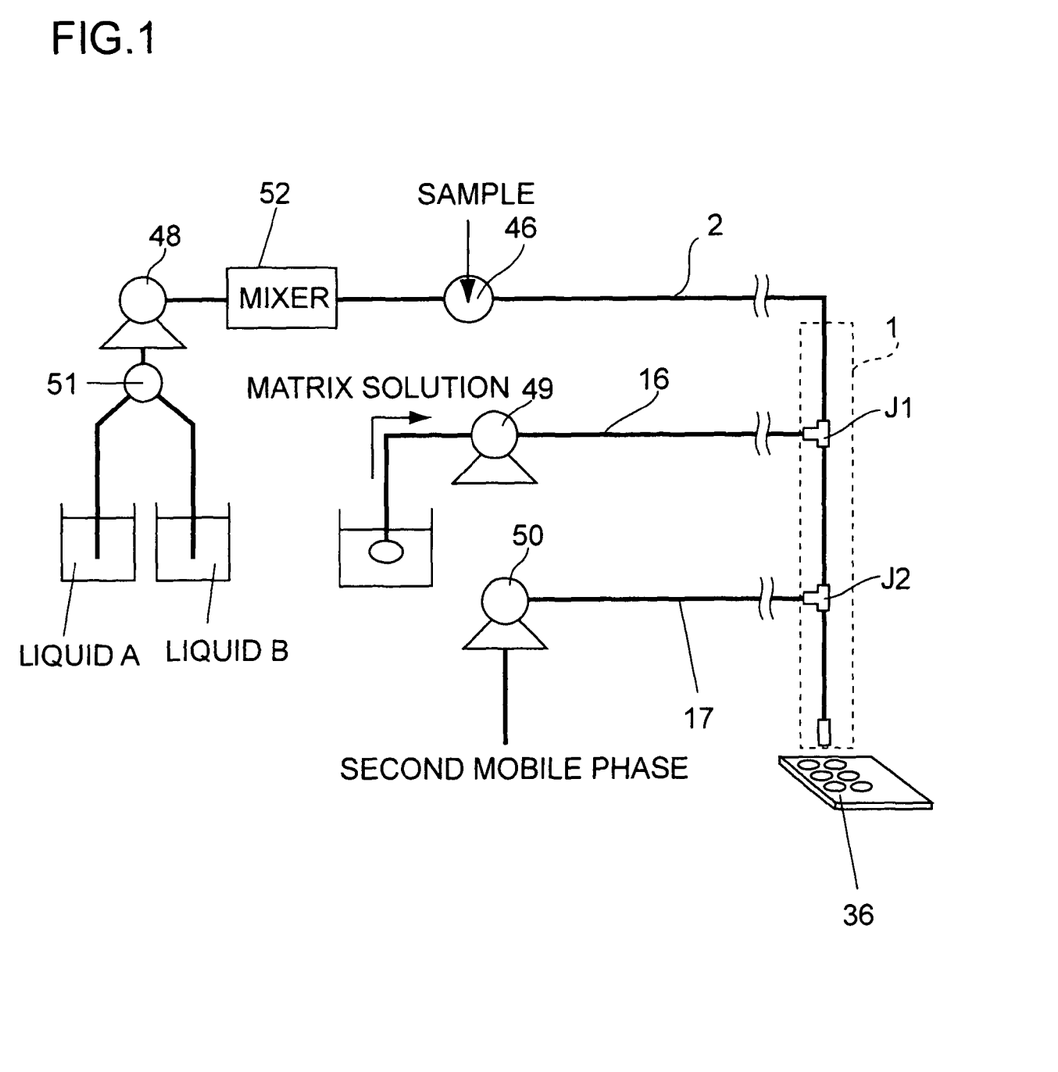
FIG. 1 is a drawing that schematically shows flow paths of one embodiment of a sample pretreatment apparatus.

FIG. 1 is a drawing that schematically shows one embodiment of a pretreatment apparatus for a MALDI-TOF-MS to which the present invention is applied.

This apparatus is provided with a flow-path switching valve 51, a liquid-transporting pump 48 and a mixer 52 as a liquid-transporting mechanism used for supplying a mobile phase to an analyzing flow path of a high-performance liquid chromatograph. This liquid-transporting mechanism, which is a gradient-system liquid-transporting mechanism, sucks a liquid 'A' and a liquid 'B' through the liquid-transporting pump 48, with the flow paths being switched by the flow-path switching valve 51, and transports the resulting liquids to the mixer 52 to be mixed therein, and further supplies these liquids to the analyzing flow path as mobile phases. As an example, the liquid 'A' and the liquid 'B' are prepared as water and acetonitrile. Not limited to the gradient system, the liquid-transporting mechanism of the present invention may also be a system using a single mobile phase.

A capillary column 2 is used as the analyzing flow path, and an injection port 46 is formed on the inlet side of the mobile phase of the capillary column 2. The capillary column 2 is extended to a probe 1, and formed into an integral part with the probe 1.

When a sample is injected into the injection port 46, it is separated by the capillary column 2, and eluted from the tip of the probe 1, and then dropped onto a sample plate 36.

Symbol J1 represents a three-way joint that allows a pipe 16 used for transporting a matrix solution as an additive solution to be joined to the probe 1. The pipe 16 is provided with a pump 49 so as to supply the matrix solution to the probe 1.

With respect to the compound to form the matrix, for example, nicotinic acid, 2-pyrazine carboxylic acid, sinapic acid (3,5-dimethoxy-4-hydroxy cinnamic acid), 2,5-dihydroxy benzoic acid, 5-methoxy salicylic acid, α-cyano-4-hydroxy cinnamic acid (CHCA), 3-hydroxy picolinic acid, diaminonaphthalene, 2-(4-hydroxyphenylazo) benzoic acid, disilanol, succinic acid, 5-(trifluoromethyl) uracil, glycerin and the like may be used.

Symbol J2 represents a three-way joint that allows a pipe 17 used for transporting a second mobile phase to be joined to the probe 1. The pipe 17, which serves as a liquid-transporting mechanism for supplying the second mobile phase, is provided with a liquid-transporting pump 50.

The liquid-transporting mechanism for the second mobile phase may be the same liquid mechanism of the gradient system as described above; however in this case, it is supposed to supply a single mobile phase.

The tip of the probe 1 has a triple-pipe structure in which an eluent from the capillary column 2, the matrix solution joined in the three-way joint J1 and the second mobile phase joined in the three-way joint J2 are mixed in the tip of the probe 1 to form droplets, and dropped onto the sample plate 36.

Figure 2:
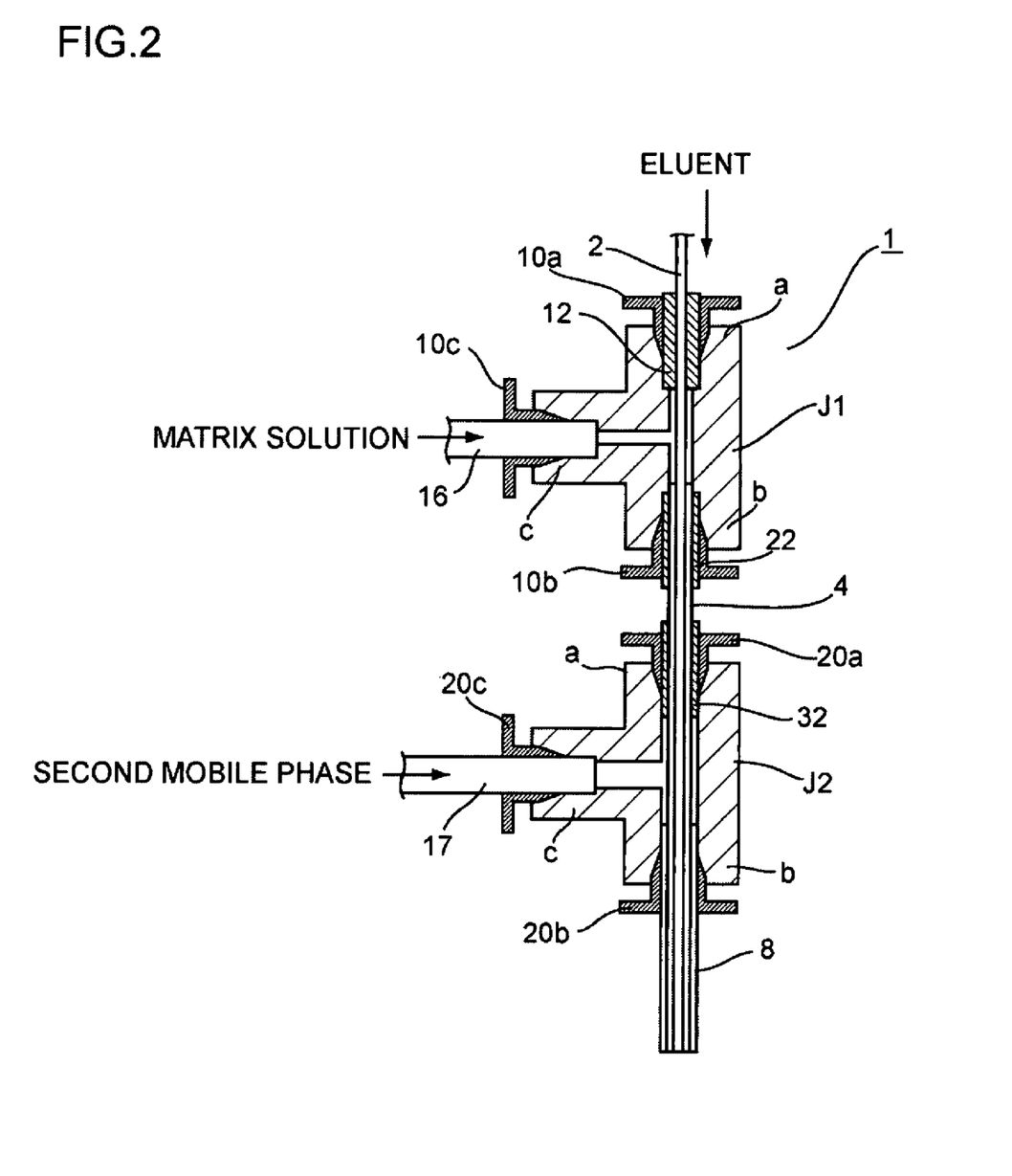
FIG. 2 is a cross-sectional view that shows a structure of a probe in accordance with the embodiment in detail.

FIG. 2 is a cross-sectional view that shows the structure of a probe portion of this embodiment in detail.

A capillary column 2 through which an eluent from a high-performance liquid chromatograph is transported is allowed to penetrate two joints 'a' and 'b', that are not orthogonally aligned, of the first T-shape three-way joint J1 on the upstream side. The joint 'a' on the upstream side is tightly sealed by using a piping member 10a such as a male nut, and in this case, a sleeve 12 or the like is used on demand.

A pipe 16 through which a matrix solution is transported is connected to a joint 'c', that is orthogonally aligned, of the T-type three way joint J1, and tightly sealed by a piping member 10c such as a male nut. The joint 'b' from which the capillary column 2 protrudes is covered with a capillary 4 on the outside of the capillary column 2, and tightly sealed by using a piping member 10b such as a male nut, and in this case, a sleeve 22 or the like is used on demand.

To a T-type three way joint J2 on the downstream side, a double capillary of the capillary column 2 and the capillary 4 is inserted from the joint 'a' on the upstream side, and tightly sealed by using a piping member 20a such as a male nut At this time, a sleeve 32 or the like is used on demand. A pipe 17 used for supplying the second mobile phase is connected to the joint 'c' that is made orthogonal to the double capillary columns 2 and 4, and tightly sealed by using a piping member 20c such as a male nut The joint 'b', located on the farthest downstream side, is covered with a pipe 8 on the outside of the capillary 4 of the double capillary columns 2 and 4, and tightly sealed by using a piping member 20b such as a male nut.

The tip of the probe 1 has a triple pipe structure including the capillary columns 2 and 4, as well as the pipe 8. An eluent from the high-performance liquid chromatograph is allowed to flow through the capillary column 2 that forms the innermost flow path, a matrix solution is allowed to flow through a flow path on the outside thereof, and the second mobile phase is allowed to flow through a flow path on the outermost side. These solutions are mixed at the tip of the probe 1 to form a droplet, and when the droplet has reached a predetermined amount, it is dropped onto the sample plate 36.

A biological sample to be analyzed by the MALDI-TOF-MS is separated by the high-performance liquid chromatograph, and dropped onto the sample plate 36 for the MALDI-TOF-MS by the present apparatus so as to be fractioned. The matrix is mixed with the mobile phase of the high-performance liquid chromatograph at the tip of the probe, and dropped onto the sample plate 36.

As an example, the flow rate of the high-performance liquid chromatograph is set to 200 nL/min (gradient of 0.1% TFA water-0.1% TFA acetonitrile), the outer diameter of the capillary column 2 is 350 μm and that the inner diameter thereof is 75 μm, with the length being set to 100 mm, the flow rate of the matrix solution is 200 nL/min and that the matrix solution is a CHCA solution with a concentration of 10 mg/mL, and the interval of spotting operations is thirty seconds. Here, TFA refers to trifluoroacetic acid.

In a case such as this ,the peak width of the target component by the capillary column 2 is thirty seconds, the interval of spotting operations is also 30 seconds so that each of the target components is spotted on the plate one component by one component, in a range of one well or two wells, without being dispersed.

Therefore, the ionizing process by the MALDI is effectively carried out on each of the target components, and even in a case of a component having a poor ionizing property, the detection can be carried out.

Figure 3:
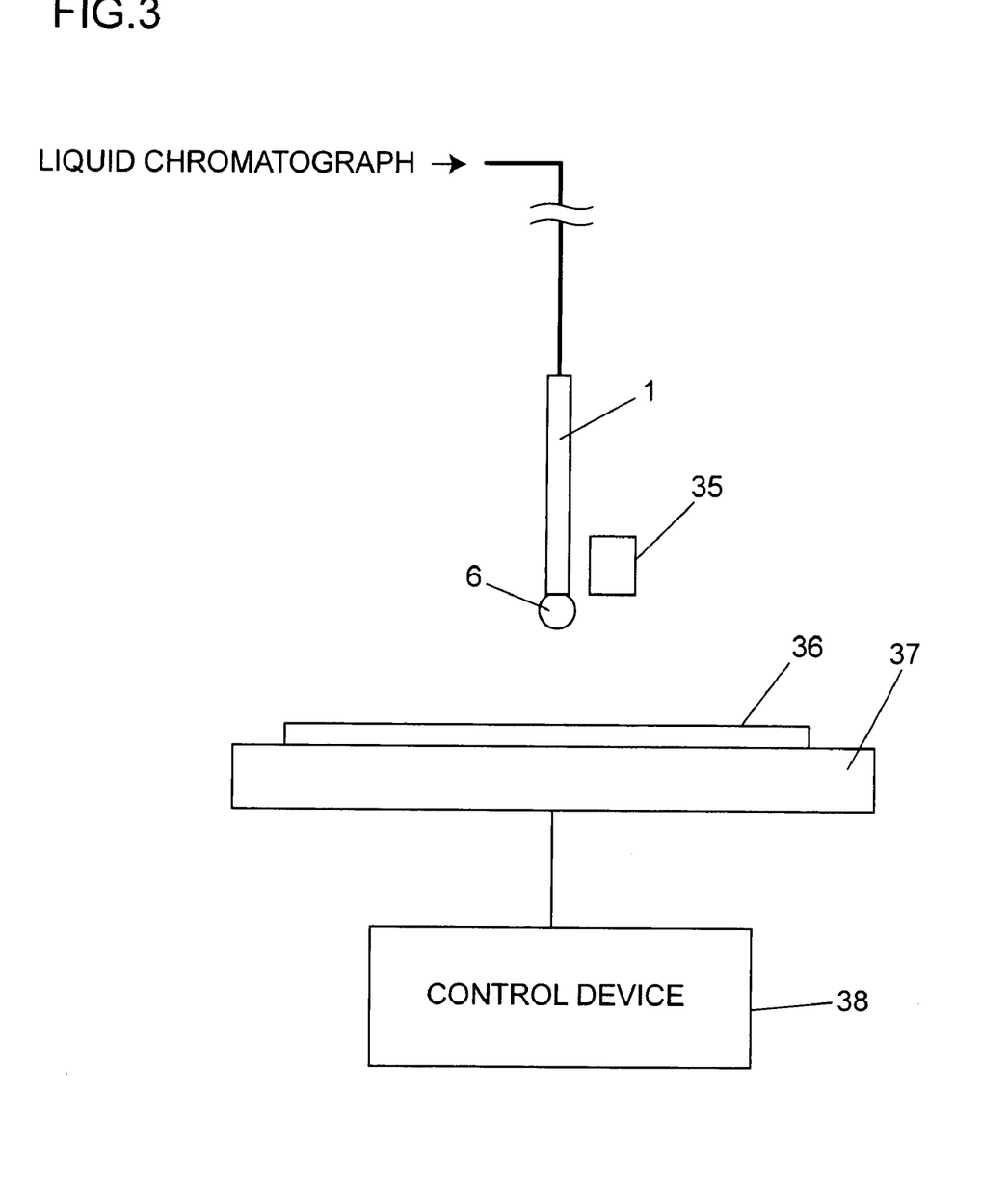
FIG. 3 is a schematic drawing that shows one embodiment relating to a supporting mechanism and a distance measuring means.

FIG. 3 is a schematic block diagram that shows one example of a fractioning device used for dropping droplets from the tip of the probe in the same embodiment.

This fractioning device is provided with a probe 1 used for dropping an eluent from the high-performance liquid chromatograph, a proximate sensor 35, serving as a distance measuring means, that is placed on the side of the tip of the probe 1, and used for measuring the distance between the tip of the probe 1 and the sample plate 36, a sample plate 36 for the MALDI-TOF-MS that is placed below the tip of the probe 1, and collects droplets 6 dropped from the probe 1, a stage 37 that moves in up and down directions as well as in directions within the plane, with the sample plate 36 being mounted thereon, and a control device 38 that controls the operations of the stage 37.

With respect to the proximate sensor 35, for example, an ultrasonic sensor and an eddy current sensor may be used. In the mass analysis of the MALDI-TOF-MS, since the amount of a sample solution required is a very fine amount, that is, 1 µL or less, in most cases, the detection distance of the proximate sensor 35 is set in a range of 1 to 1.5 mm.

The sample plate 36, mounted on the stage 37, is shifted in up and down directions, as well as in directions within the plane. Normally, with respect to the sample plate 36, for example, 192 or 384 dropping positions are determined, and droplets 6 containing the sample components are dropped onto these dropping positions by the probe 1.

The control device 38 controls the movements of the stage 37, and with respect to the controlling operations, the following two operations are conducted:

(1) Inner plane control in which the stage 37 is moved within the horizontal plane so as to be positioned so that the droplets are precisely dropped onto predetermined dropping positions on the sample plate 36.

(2) Longitudinal direction control in which the stage 37 is controlled to make the sample plate 36 come close to the probe 1 so that the droplet 6, formed on the tip of the probe 1 at the time of dropping the droplet, is made to come in contact with the dropping position of the sample plate 36.

In place of the sample plate 36 for the MALDI-TOF-MS, a sample plate for an FT IR may be mounted on the stage 37, and the same effects can be obtained in this case also.

The amount of droplets to be dropped from the probe 1 may be desirably altered.

Further, the detection point of the proximate sensor 35 may be desirably set by the operator. Moreover, the initial position of the sample plate 36 may be as desired altered.

Normally, in the HPLC used for separating and analyzing a biological sample, the analysis is carried out by the gradient method, and a low value in the organic solvent concentration is selected as the initial value of a mobile phase composition, with the result that the rate of water becomes higher in the mobile phase components. Since water has high surface tension, there is a strong tendency that when the rate of water in the mobile phase is high, droplets coming out of the tip of the probe rise along the outside of the probe.

A contact angle may be used as a standard by which the hydrophobicity and/or hydrophilicity of a substance are evaluated, and the greater the contact angle, the stronger the hydrohobicity becomes.

A preferable example of the hydrophobic material is a fluororesin. With respect to the fluororesin, in addition to ethylene tetrafluoride resin (PTFE), various fluororesins obtained by modifying this can be used. With respect to such modified fluororesins, in addition to ethylene tetrafluoride-propylene hexafluoride resin (FEP) and ethylene tetrafluoride-perfluoroalkoxy ethylene copolymer resin (PFA), ethylene tetrafluoride-ethylene copolymer resin (ETFE) and the like may be used.

In general, PEEK (polyether-ether ketone), which has the greatest contact angle among the materials used for a probe, has a contact angle of about 88 degrees, while FEP has a contact angle of about 120 degrees. In this embodiment, by using an FEP tube as the capillary 4 serving as the outermost pipe that is made in contact with droplets, it is possible to provide superior hydrophobicity, and droplets of the mixed solution between a mobile phase from the high-performance liquid chromatograph and a matrix solution are hardly transmitted to the outside of the capillary 4 so that uniform droplets can be formed at the tip of the probe 1; thus, each droplet comes in contact with the sample plate 36 as the stage is raised so that the droplets are uniformly fractioned on the sample plate 36. Here, the capillary column 2 is made from fused quartz and the pipe 8 on the outermost side of the probe is made of stainless steel.

The following description will discuss an embodiment in which the second mobile phase is improved.

In the gradient analysis, the components in the droplets are different between a state immediately before the start of distribution and a state immediately after the completion of distribution. For example, in a case of a gradient analysis in which a large water component is contained in a state immediately before fractioning, while a large amount of acetonitrile is contained in a state immediately after the completion of distribution, the surface tension of the droplets formed at the tip of the probe is varied, resulting in a failure to form droplets having a uniform size.

Moreover, in a case where a matrix solution is added to an eluent from a separation column at the tip of the probe so as to be distributed from the tip, a hydrophobic substance such as a fluororesin is used as the material for the matrix adding pipe of the probe portion so as to prevent the droplets from rising along the matrix adding pipe. For this reason, since the droplet contains a large water component immediately after the start of distribution, the droplet is formed on the inner diameter side of the matrix adding pipe. However, since the droplet contains a large amount of acetonitrile immediately before the completion of distribution, the droplet is formed on the outer diameter side of the matrix adding pipe. Here, in a case where the volume of the droplets is constant, the outer shapes of droplets formed at the tip of the probe are made different between a state immediately before the start of distribution and a state immediately after the completion of distribution. In other words, since the droplets formed at the tip of the probe have different heights in the direction toward the sample plate, even in a case of having a sensor used for keeping the distance between the tip of the probe and the sample plate constant, the droplet is not made in contact with the sample plate, in particular, in a case where the amount of the droplet is very small, sometimes resulting in a failure to shift the droplet to the sample plate.

Figure 4A:
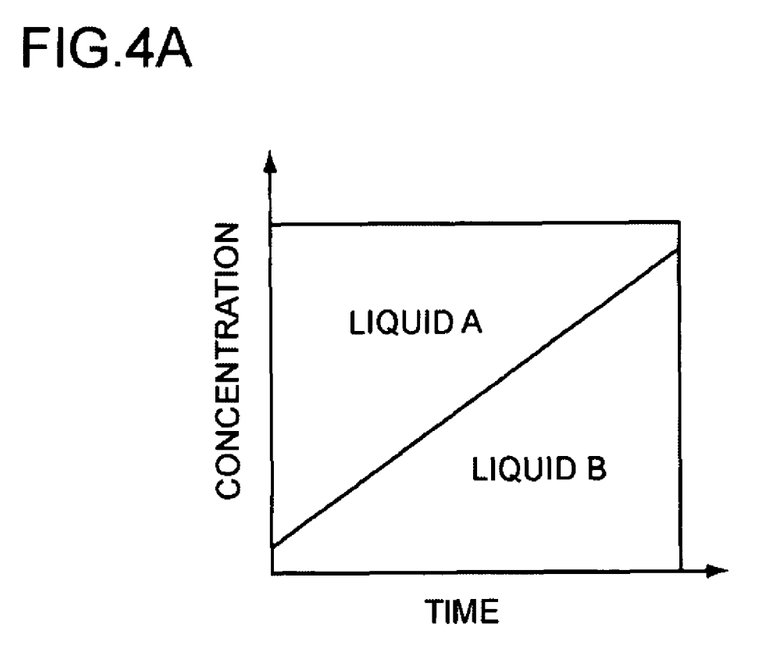
FIG. 4A is a drawing that shows a time-based change in the composition of the first mobile phase.
Figure 4B:
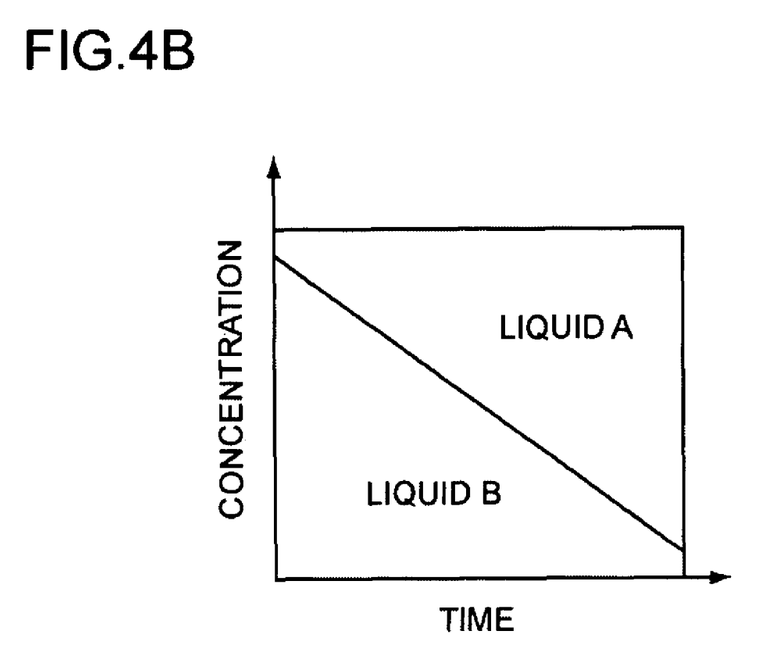
FIG. 4B is a drawing that shows a time-based change in the composition of the second mobile phase.

FIG. 4A and FIG. 4B show a time-based change in the composition between a mobile phase (first mobile phase) and the second mobile phase, which are transported by the pump 48. FIG. 4A is a drawing that shows a time-based change in the composition of the first mobile phase, and FIG. 4B is a drawing that shows a time-based change in the composition of the second mobile phase.

Figure 5:
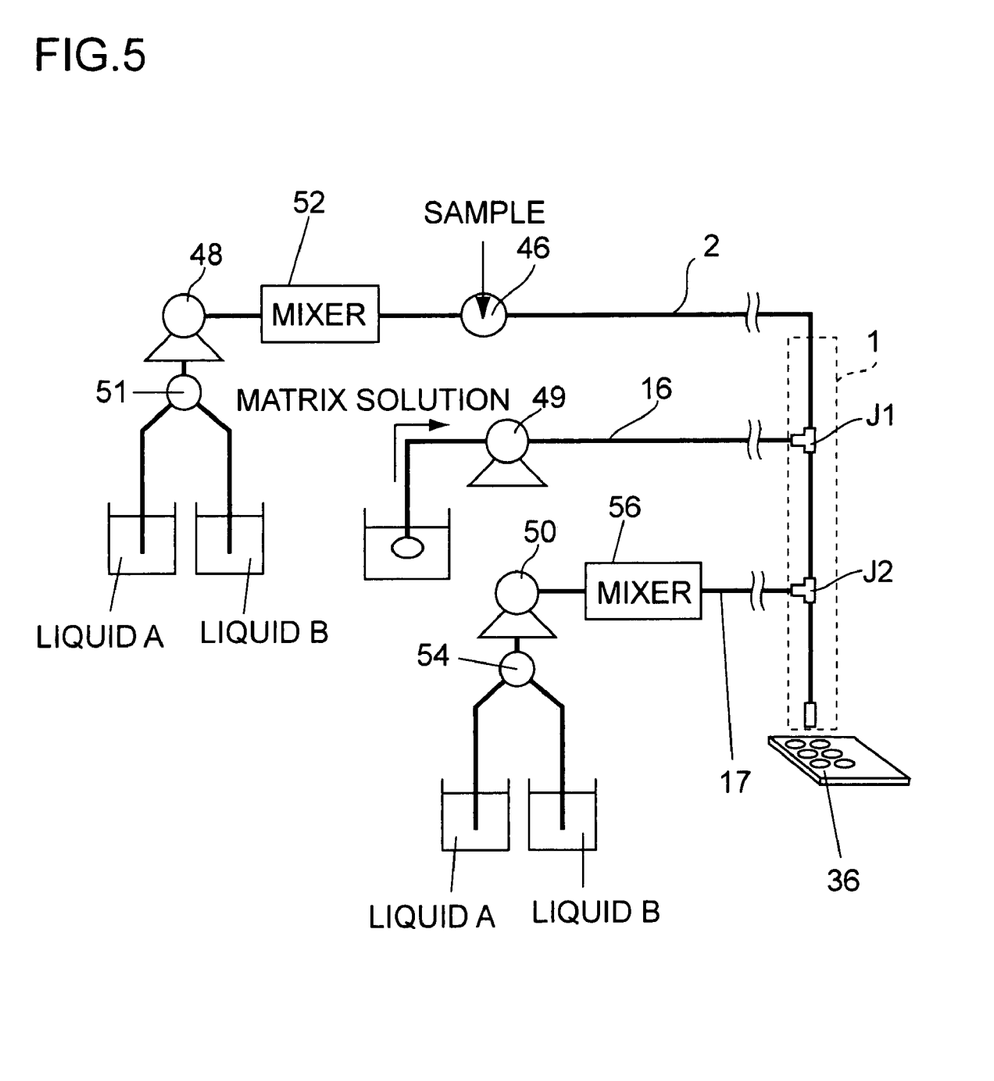
FIG. 5 is a diagram that schematically shows flow paths of another embodiment of a sample pretreatment apparatus.

A second mobile phase supplying flow path, which supplies the second mobile phase, is shown in FIG. 5. The pipe 17, which transports the second mobile phase, is provided with a flow-path switching valve 54, a liquid-transporting pump 50 and a mixer 56 as a liquid-transporting mechanism used for supplying the second mobile phase.

The liquid-transporting mechanism for the second mobile phase is the same gradient-system liquid-transporting mechanism as the first mobile phase supplying flow path 2, which sucks a liquid 'A' and a liquid 'B' through a liquid-transporting pump 48, with the flow paths being switched by the flow-path switching valve 51, and transports the resulting liquids to a mixer 52 to be mixed therein, and further supplies these liquids to the analyzing flow path as mobile phases. The mixing ratio of the liquid 'A' and the liquid 'B' to be mixed in the mixer 56 is adjusted so as to be reversed to the mixing ratio of the liquid 'A' and the liquid 'B' mixed in the mixer 52 used for forming the first mobile phase used for separation.

As shown in FIG. 4A, immediately after the start of distribution, with respect to the first mobile phase, the percentage of the liquid 'A' (water) occupies most of the solution; however, the rate of the liquid 'B' linearly increases with time. In contrast, as shown in FIG. 4B, immediately after the start of distribution, with respect to the second mobile phase, the percentage of the liquid 'B' (acetonitrile) occupies most of the solution; however, the percentage of the liquid 'A' linearly increases with time.

The second mobile phase is adjusted in its composition so that the mixed solution of the first mobile phase and the second mobile phase is always set to liquid 'A':liquid 'B'=1: 1.

For example, after a lapse of a certain period of time since the start of distribution, the composition of the first mobile phase has changed to 90% of the liquid 'A' and 10% of the liquid 'B', the second mobile phase is adjusted to 10% of the liquid 'A' and 90% of the liquid 'B'. Therefore, the eluent mixed with the second mobile phase at the tip of the probe 1 has a mixing ratio of water or acetonitrile indicated by: water: acetonitrile=1:1.

Here, the MALDI-TOF-MS analysis is carried out on the premise that the amount of droplets to be distributed is a fine amount with a constant value; therefore, when the composition of the mobile phase in the droplet is varied as described above, the shape of the droplet formed at the tip of the probe is also varied. Consequently, since the distance between the tip of the probe and the tip of the droplet becomes longer immediately after the start of distribution, and since the distance between these immediately before the completion of the distribution becomes shorter, the difference between the distances becomes conspicuous, in particular, when the set amount of the droplets to be distributed is small, sometimes resulting in a failure to move the droplet onto the plate by the use of the predetermined distance between the probe and the plate.

In the present embodiment, since the composition of the mobile phase inside the droplet to be formed at the tip of the probe is made constant, the size (height) of the droplet to be formed on the tip of the probe is consequently made constant so that the distributing operation can be carried out stably.

Figure 6:
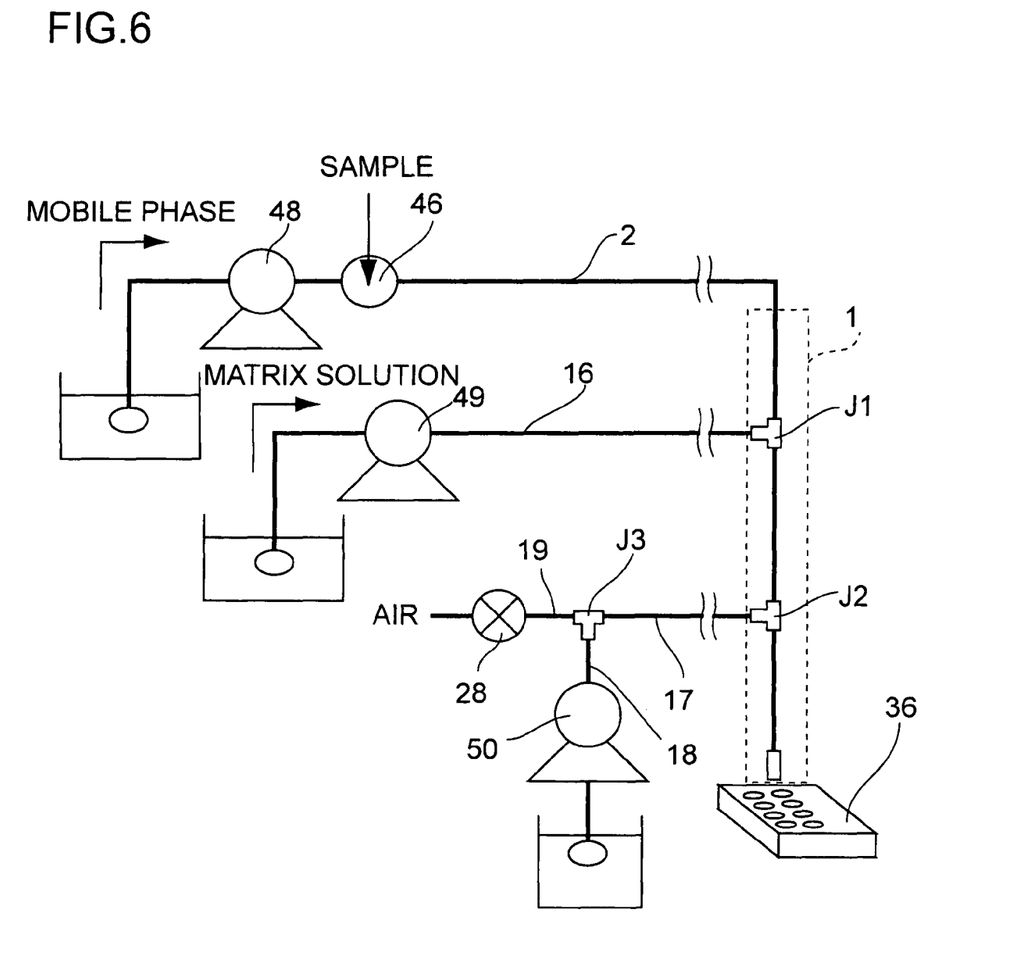
FIG. 6 is a diagram that schematically shows flow paths of the other embodiment of a sample pretreatment apparatus.
Figure 7:
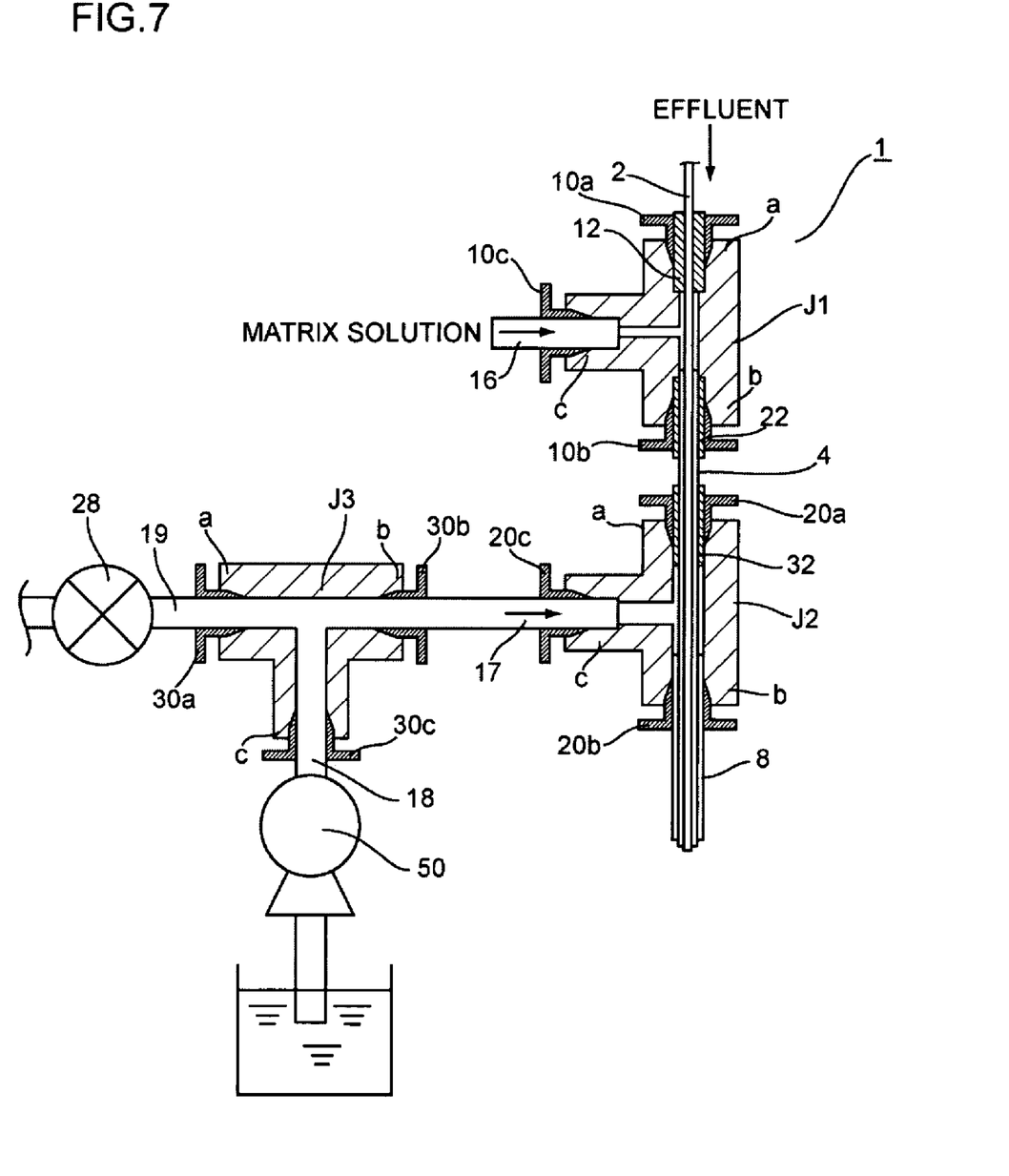
FIG. 7 is a cross-sectional view that shows the structure of a probe in accordance with the embodiment.

Next referring to FIGS. 6 and 7, the following description will discuss still another embodiment of the present invention.

Time consuming and complicated operations are required upon manually washing the tip of the probe prior to fractioning operations, and the operability is also poor; therefore, there has been a demand that the deposition onto the tip of the probe upon addition of the matrix solution thereto can be automatically washed. For this reason, an arrangement is made so that an air flow and a washing liquid are switched and allowed to flow through the pipe on the outermost side of the probe.

In FIG. 6, the capillary column 2 is connected along the flow path of the pump 48 used for transporting the mobile phase and the injection port 46 used for injecting the sample.

With respect to the analyzing flow path, the capillary column 2 is used in the same manner as the embodiment explained by reference to FIG. 1, and the injection port 46 is placed on the inlet side for the mobile phase of the capillary column 2. The capillary column 2 is extended to the probe 1, and formed as an integral part with the probe 1.

The probe 1 is provided with T-type three-way joints J1 and J2. The joint J1 on the upstream side connects the capillary column 2 used for transporting the mobile phase to the pipe 16 used for transporting a matrix solution, and the joint J2 on the downstream side connects it to the pipe 17 used for supplying air and acetone serving as a washing liquid, with the tip of the probe 1 on the outlet side being formed into a triple pipe structure.

A sample, which has been injected to the injection port 46, is separated by the capillary column 2 and eluted from the tip of the probe 1, and then dropped onto the sample plate 36.

With respect to the matrix compound to be added to the mobile phase, the same compound as explained in the first embodiment may be used. With respect to the washing liquid used for dissolving this matrix compound, organic solvents, such as acetone and acetonitrile, are used.

The matrix solution is transported by the pump 49 through the pipe 16 connected to the capillary column 2 via the T-type three-way joint J1 and allowed to flow outside of the capillary column 2 to reach the tip of the probe 1 so that it is dropped from the tip of the probe 1 simultaneously with the mobile phase containing the sample components.

The air supplying pipe 19 and the washing liquid supplying tube 18 are jointed together by a T-type three-way joint J3, and allowed to flow through the pipe 17 forming the common flow path of these. The pipe 17 is connected to the capillary column 2 through which the mobile phase flows as well as to the pipe through which the matrix solution flows by the T-type three-way joint J2 so that the air and the washing liquid are allowed to flow further outside the pipe through which the matrix solution flows.

Here, with respect to the matrix solution, for example, a saturated solution (10 mg/mL), prepared by dissolving CHCA (α-cyano-4-hydroxy cinnamic acid) in a mixed solution of water and acetonitrile, is used, and with respect to the washing liquid, for example, acetone is used.

A valve 28 is attached to the air supplying pipe 19 so that the air supply is controlled by the opening and closing operations of the valve 28. A pump 50 is attached to the washing solution supplying pipe 18, and acetone serving as the washing liquid is allowed to flow through the washing solution supplying pipe 18 to be supplied to the probe 1 by the operation of the pump 50.

Upon dropping the mobile phase from the liquid chromatograph, the matrix solution is also dropped from the tip of the probe 1 onto the sample plate 36 simultaneously with the mobile phase. Since, after the liquid has been dropped, the matrix compound tends to be deposited on the tip of the probe 1, acetone serving as washing liquid is supplied to the tip of the probe 1 through the washing-liquid supplying pipe 18 so that the tip of the probe 1 is washed. In order to prevent the washing liquid from remaining on the tip of the probe 1, after the tip of the probe 1 has been washed, air is supplied to the tip of the probe 1 by opening the valve 28 so that the residual washing liquid on the tip of the probe 1 is evaporated.

FIG. 7 is a cross-sectional view that shows the probe of the present embodiment in detail.

The capillary column 2, which is the narrowest, and through which the mobile phase is transported from the high-performance liquid chromatograph, crosses two joints a and b of the first T-type three-way joint J1 on the upstream side, which are not orthogonally aligned. The joint 'a' on the upstream side is tightly sealed by using a piping member 10a, such as a male nut, through a sleeve 12.

To the T-type three-way joint J2 on the downstream side, the capillary columns 2 and 4 are inserted from the joint 'a' on the upstream side and tightly sealed by using a piping member 20a such as a male nut through a sleeve 32. To the joint 'c' that is orthogonal to the capillary columns 2 and 4, the pipe 17 which supplies air and acetone serving as washing liquid, is connected, and tightly sealed by using a piping member 20c such as a male nut. On the joint 'b' on the furthest downstream side, the capillary columns 2 and 4 are covered with a pipe 8, and tightly sealed by using a piping member 20b such as a melt nut.

To the T-type three-way joint J3 located on the side of the T-type three-way joint J2, an air supplying pipe 19 is inserted from the joint 'a', a pipe 17 which is connected to the T-type three-way joint J2 from the joint 'c', is inserted from the joint 'b', and the washing liquid supplying pipe 18 is inserted from the joint 'c', with the respective pipes 19, 17 and 18 being tightly sealed by using piping members 30a, 30b and 30c, such as male nuts.

To the T-type three-way joint J3 located on the side of the T-type three-way joint J2, an air supplying pipe 19 is inserted from the joint 'a', a pipe 17 which is connected to the T-type three-way joint J2 from the joint 'b', is inserted from the joint 'b', and the washing liquid supplying pipe 18 is inserted from the joint 'c', with the respective pipes 24, 18 and 26 being tightly sealed by using piping members 30a, 30b and 30c such as male nuts.

A valve 28 is attached to the air supplying pipe 19 so that the supply of air to the tip of the probe 1 is switched on/off by opening and closing the valve 28. A pump 50 is attached to the washing liquid supplying pipe 18 so that acetone to be supplied to the tip of the probe 1 through the pipe 17 is switched on/off by the on/off operations of the pump 50.

Here, the matrix solution is a solution prepared by dissolving a matrix compound that is a fat-soluble substance in a solvent at a high concentration; therefore, while fractioning processes are continuously carried out by allowing the liquid chromatograph to separate a sample to be eluted, with the matrix solution being simultaneously added thereto while the resulting solution is dropped, the matrix solution comes in contact with the atmosphere at the tip of the probe so that the solvent is evaporated to cause the matrix compound to be deposited on the tip of the probe.

Then, after the completion of the analysis or before the next analyzing process, the pump 50 is operated so that acetone of, for example, 200 µL is transported, and the tip of the probe 1 is washed with acetone. The acetone, sent out by the pump 50, is allowed to flow between the double pipe and the triple pipe of the probe 1 through the T-type joint J3 to be connected to a gas line for drying and evaporating so that the matrix compound stuck on the tip of the probe 1 is washed away. Thereafter, the gas valve 28 for drying and evaporating is opened so that residual acetone is evaporated.

As in this example, where the air supplying pipe 19 and the washing liquid supplying pipe 18 are connected by using the T-type joint as described in this embodiment, the flow path resistance is preferably adjusted so as to prevent the washing liquid, such as acetone, from reversely flowing toward the gas valve 28 side. For example, a pipe having an inner diameter of 0.1 mm and a length of about 100 mm is used as the air supplying pipe 19.

In place of the T-type joint J3, a three-way electromagnetic valve may be used, and in that case, it is not necessary to take the reverse flow of the washing liquid toward the gas valve 28 side into consideration.

In this embodiment, since the washing liquid flow path is prepared so as to send the washing liquid toward the tip of the probe, the matrix compound deposited on the tip of the probe can be automatically removed.

The present invention embodiment has been explained by exemplifying a high-performance liquid chromatograph with a probe having a triple pipe structure; however, the present invention can be applied to a probe having a multi-pipe structure other than the double or triple pipe structure.

The present is applicable to a pretreatment in which a sample, for example, a sample for the MALDI-TOF-MS, is adjusted by dropping a sample solution eluted from a liquid-transporting mechanism such as a high-performance liquid chromatograph as droplets onto a plate such as a micro-plate from the tip thereof.

The invention claimed is:

1. A probe which forms a droplet containing an effluent and an additive solution, and allows the droplet to drop from a tip thereof, comprising a triple pipe structure in which a plurality of pipes are placed concentrically,
    wherein the triple pipe structure comprises:
    (a) a pipe that is placed on an innermost side of the structure, and forms a tip of a capillary column used for separation in a micro-scale or nano-scale high-performance liquid chromatograph;
    (b) an additive supplying pipe placed as a second pipe from the inside, the additive supplying pipe being used for allowing the additive solution to be joined to the effluent from the capillary column; and
    (c) a mobile phase supplying pipe placed on an outermost side of the structure, through the mobile phase supplying pipe a second mobile phase, different from a mobile phase in the eluent, being allowed to flow;
    and the droplet contains the eluent, the additive and the second mobile phase.

2. The probe according to claim 1, wherein the second mobile phase is mixed with the mobile phase in the eluent so that the composition of the mobile phase in the droplet is made constant.

3. The probe according to claim 1, wherein the pipe on an outermost side of the multiple pipes, which is made in contact with the droplet, is made from a hydrophobic material.

4. The probe according to claim 3, wherein the hydrophobic material is a fluororesin.

5. A probe which forms a droplet containing an effluent and an additive solution, and allows the droplet to drop from a tip thereof, comprising a triple pipe structure in which a plurality of pipes are placed concentrically,
    wherein the triple pipe structure comprises:
    (a) a pipe that is placed on an innermost side of the structure, and forms a tip of a capillary column used for separation in a micro-scale or nano-scale high-performance liquid chromatograph;
    (b) a mobile phase supplying pipe placed as a second pipe from the inside, through the mobile phase supplying pipe a second mobile phase, different from a mobile phase in the eluent, being allowed to flow; and
    (c) an additive supplying pipe placed on an outermost side of the structure, the additive supplying pipe being used for allowing the additive solution to be joined to the effluent from the capillary column;
    and the droplet contains the eluent, the additive and the second mobile phase.

6. The probe according to claim 5, wherein the second mobile phase is mixed with the mobile phase in the eluent so that the composition of the mobile phase in the droplet is made constant.

7. The probe according to claim 5, wherein the pipe on an outermost side of the multiple pipes, which is made in contact with the droplet, is made from a hydrophobic material.

8. The probe according to claim 7, wherein the hydrophobic material is a fluororesin.

9. A sample pretreatment apparatus comprising:
a micro-scale or nano-scale high-performance liquid chromatograph provided with a capillary column;
a probe, integrally formed on a tip of the capillary column, which has a triple pipe structure in which a plurality of pipes are placed concentrically,
the triple pipe structure comprising (a) a pipe placed on an innermost side of the structure that forms the tip of the capillary column, (b) an additive supplying pipe used for allowing an additive solution to be joined to an eluent from the capillary column as a second pipe from the inside of the structure, and (c) a mobile phase supplying pipe placed on an outermost side of the structure, through the mobile phase supplying pipe a second mobile phase different from a mobile phase in the eluent is allowed to flow, so that droplets containing the eluent, the additive solution and the second mobile phase are formed and dropped from a tip of the probe;
a mobile phase supplying flow path used for supplying the second mobile phase to the mobile phase supplying pipe; and
an additive supplying flow path used for supplying the additive solution to the additive supplying pipe.

10. The sample pretreatment apparatus according to claim 9, wherein the second mobile phase is mixed with the mobile phase in the eluent so that the composition of the mobile phase in the droplets is made constant.

11. The sample pretreatment apparatus according to claim 9, wherein the pipe on the outermost side of the multiple pipes, which is made in contact with the droplets, is made from a hydrophobic material.

12. The sample pretreatment apparatus according to claim 11, wherein the hydrophobic material is a fluororesin.

13. The sample pretreatment apparatus according to claim 9, further comprising:
a supporting mechanism that shifts a plate or the probe at least in up and down directions, the plate being used for collecting droplets dropped from the probe;
distance measuring means for measuring a distance between the tip of the probe and the plate; and
a control unit that controls the shift of the supporting mechanism so as to set the distance between the tip of the probe and the plate to a predetermined distance based upon the results of measurements by the distance measuring means upon dropping droplets from the probe.

14. The sample pretreatment apparatus according to claim 9, wherein the additive solution is a solution for a matrix compound, used for preparing a sample for use in ain analysis in mass spectrometry by a Matrix assisted laser desorption ionization time of flight method.

15. A sample pretreatment apparatus comprising:
a micro-scale or nano-scale high-performance liquid chromatograph provided with a capillary column;
a probe, integrally formed on a tip of the capillary column, which has a triple pipe structure in which a plurality of pipes are placed concentrically,
the triple pipe structure comprising (a) a pipe placed on an innermost side of the structure that forms the tip of the capillary column, (b) a mobile phase supplying pipe as a second pipe from the inside of the structure, through the mobile phase supplying pipe a second mobile phase different from the mobile phase in the eluent is allowed to flow, and (c) an additive supplying pipe used for allowing an additive solution to be joined to an eluent from the capillary column as an outermost side of the structure, so that droplets containing the eluent, the second mobile phase and the additive solution are formed and dropped from a tip of the probe;
a mobile phase supplying flow path used for supplying the second mobile phase to the mobile phase supplying pipe; and
an additive supplying flow path used for supplying the additive solution to the additive supplying pipe.

16. The sample pretreatment apparatus according to claim 15, wherein the second mobile phase is mixed with the mobile phase in the eluent so that the composition of the mobile phase in the droplets is made constant.

17. The sample pretreatment apparatus according to claim 15, wherein the additive solution is a solution for a matrix compound, used for preparing a sample for use in an analysis in mass spectrometry by a Matrix assisted laser desorption ionization time of flight method.

18. The sample pretreatment apparatus according to claim 15, wherein the pipe on the outermost side of the multiple pipes, which is made in contact with the droplets, is made from a hydrophobic material.

19. The sample pretreatment apparatus according to claim 18, wherein the hydrophobic material is a fluororesin.

20. The sample pretreatment apparatus according to claim 15, further comprising:
a supporting mechanism that shifts a plate or the probe at least in up and down directions, the plate being used for collecting droplets dropped from the probe;
distance measuring means for measuring a distance between the tip of the probe and the plate; and
a control unit that controls the shift of the supporting mechanism so as to set the distance between the tip of the probe and the plate to a predetermined distance based upon the results of measurements by the distance measuring means upon dropping droplets from the probe.

* * * * *